United States Patent [19]
Brion et al.

[11] Patent Number: 5,585,482
[45] Date of Patent: Dec. 17, 1996

[54] PREPARATION OF 11-KETO STEROIDS

[75] Inventors: Francis Brion, Gagny; Jean Buendia, Le Perreux Sur Marne; Christian Diolez, Palaiseau; Michel Vivat, Lagny Sur Marne, all of France

[73] Assignee: Roussel Uclaf, France

[21] Appl. No.: 545,518

[22] Filed: Oct. 19, 1995

Related U.S. Application Data

[63] Continuation of Ser. No. 386,692, Feb. 10, 1995, abandoned, which is a continuation of Ser. No. 68,253, May 27, 1993, abandoned.

[30] Foreign Application Priority Data

Jun. 4, 1992 [FR] France ................................. 92 06773

[51] Int. Cl.⁶ .................................. C07J 33/00; C07J 5/00
[52] U.S. Cl. ............................ 540/30; 552/577; 552/579
[58] Field of Search ................................ 552/577; 540/30

[56] References Cited

FOREIGN PATENT DOCUMENTS

| 536948 | 2/1957 | Canada | 552/577 |
| 931577 | 7/1963 | United Kingdom | 552/577 |

*Primary Examiner*—Rebecca Cook
*Attorney, Agent, or Firm*—Bierman and Muserlian

[57] ABSTRACT

A process for the preparation of a compound of the formula

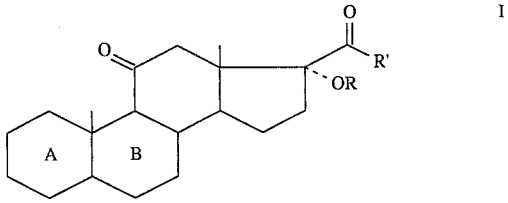

wherein R and R' and the A and B are as defined in the specification.

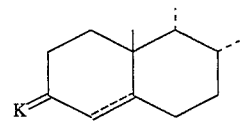

K is selected from the group consisting of

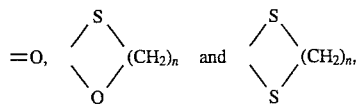

n is 2 or 3 and the dotted lined is an optional bond.

9 Claims, No Drawings

PREPARATION OF 11-KETO STEROIDS

PRIOR APPLICATION

This application is a continuation of U.S. patent application Ser. No. 386,692 filed Feb. 10, 1995 which is a continuation of U.S. patent application Ser. No. 068,253 filed May 27, 1993, both now abandoned.

European patent No. 30,368 describes the preparation of 11-keto steroids by heating a 9α-halo-11-β-ol steroid at 180° to 350° C., preferably 250° to 300° C. in the presence of an aprotic solvent with a high boiling point for a short period, i.e. a few minutes. The solvent is preferably biphenyl, dibenzofuran, diphenylene oxide or methyl ether of polyalcohols. However, the use of such high temperatures for a short period of time is not industrially feasible.

OBJECTS OF THE INVENTION

It is an object of the invention to provide a novel process for the preparation of 11-keto steroids under mild, industrial conditions.

This and other objects and advantages of the invention will become obvious from the following detailed description.

THE INVENTION

The novel process of the invention for the preparation of a compound of the formula

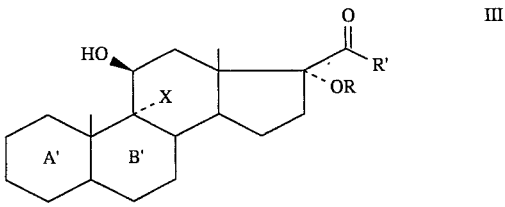

wherein R is selected from the group consisting of hydrogen, an ester group and an ether group, R' is methyl or —CH$_2$OR", R" is hydrogen or an ether group or ester group the same as or different from R and rings A and B are

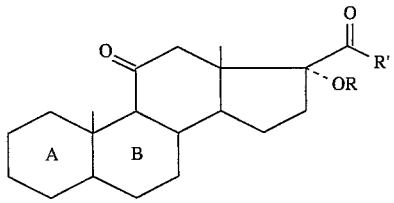

K is selected from the group consisting of

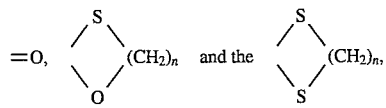

n is 2 or 3 and the dotted lined is an optional bond comprises reacting a compound of the formula

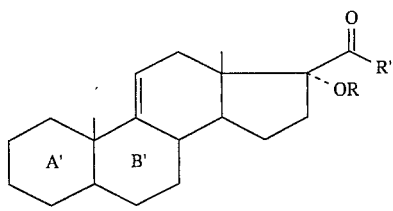

wherein R and R' have the above definitions and A' and B' are selected from the group consisting of A and B as above,

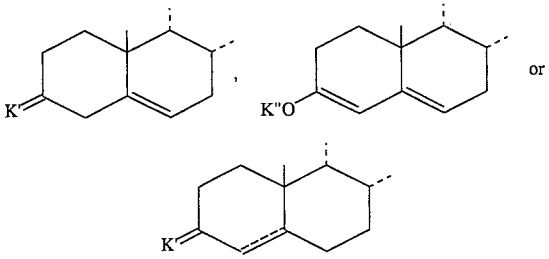

K' is

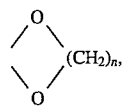

n is 2 or 3 and K" is alkyl of 1 to 8 carbon atoms or aryl of 6 to 12 carbon atoms with a halogenating agent to form a compound of the formula

III

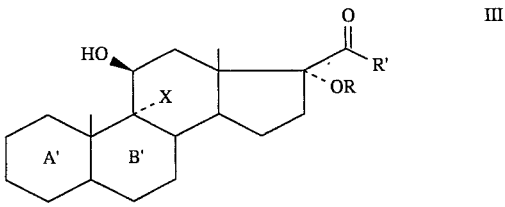

wherein R, R', A' and B' have the above definitions and X is halogen, subjecting the latter to a rearrangement in the presence of an alcohol and then to an acid treatment to obtain a compound of formula I.

Examples of halogen are bromine, chlorine and iodine with bromine being preferred. When R and R" are an ester remainder, they are preferably an acyl of an organic carboxylic acid of 1 to 8 carbon atoms and more particularly formyl, acetyl, propionyl, butyryl, valeryl or benzoyl. When R and R" are an ether remainder, they are preferably alkyl of 1 to 6 carbon atoms, for example methyl, ethyl or propyl, tetrahydropyranyl, or a silylated ether remainder such as trialkylsilyl like trimethyl- or dimethylterbutylsilyl or triarylsilyl such as triphenylsilyl or diarylalkylsilyl such as diphenylterbutylsilyl.

When K" is alkyl, it is preferably methyl or ethyl and when K" is aryl, it is preferably phenyl. In the process of the invention, the rearrangement reaction is preferably carried out in the presence of a higher alcohol or a polyalcohol. The higher alcohol or polyalcohol is preferably selected from the group consisting of glycerol, ethylene glycol and propylene glycol, ethylene glycol being particularly preferred.

The operation is preferably carried out in the presence of an excess of the alcohol or the polyalcohol by heating to a temperature lower than 100° C. By excess is preferably meant 10 to 20 equivalents. In addition, the operation is advantageously carried out in the presence of a cosolvent which is inert under the reaction conditions and with a boiling point less than 100° C., and at reflux of the cosolvent. The cosolvent is for example an ester such as ethyl acetate, benzene or cyclohexane with ethyl acetate being preferred.

The subsequent acid treatment is preferably carried out with an aqueous mineral or organic acid such as hydrochloric acid, hydrobromic acid, sulfuric acid, perchloric acid, nitric acid, p-toluenesulfonic acid, acetic acid, formic acid, oxalic acid, or also with an acid resin.

In particular, the result of the acid treatment is to unblock the ketal formed intermediately in position 20 and, if appropriate, in position 3, by the action of the alcohol. Another result when a compound of formula II in which rings A' and B' are different from A and B is used at the start of the process, and only in this case, is to free the 3-keto-$\Delta^4$ system or the 3-keto function.

In the compounds of formula III, X is preferably bromine and A' and B' rings are

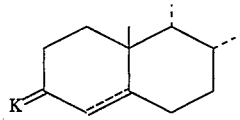

R and R" are individually preferably selected from the group consisting of hydrogen, acyl of an organic carboxylic acid of 2 to 8 carbon atoms, alkyl of 1 to 6 carbon atoms, tetrahydropyranyl and a silylated ether and R is methyl or —$CH_2OR$".

The process of the invention has much more moderate operating conditions than European patent No. 30,368, possibly due to the use of intermediates blocked in situ at the ketone functions. It is possibly that the result may be due to the blocking which appears to be the labilization of the carbon-halogen bond in position 9, which facilitates rearrangement and therefore allows the use of very moderate operating conditions. In practice, this corresponds to operating at a temperature lower than 100° C., and is achieved due to the use of an appropriate cosolvent.

The process of European Patent 30,368 does not anticipate the formation of the intermediates used in the process of the invention which is why it requires different operating conditions to obtain the desired result. In addition, it is evident that such a process which requires the halohydrin to be subjected to a very high heat for a short period is hardly foreseeable at an industrial level where high tonnages are used. On the other hand, the process of the invention easily permits industrial synthesis. In addition, using much more moderate conditions than those described in European Patent No. 30,368, this is an advantage with regard to the yield of the reaction, because the formation of secondary products or degradation products is inevitably limited, therefore also an advantage at the industrial level, in so far as the synthesis is all the more economical.

The halohydrins of formula III are known or can be easily prepared by processes known to one skilled in the art. By way of example the following references can be mentioned: J.A.C.S., Vol. 79, p. 1135 (1957), U.S. Pat. Nos. 2,763,671, 2,852,511 or U.S. Pat. No. 2,963,498, BF 1 188 434, U.S. Pat. Nos. 3,100,210, 3,084,174 or U.S. Pat. No. 3,499,081, EP 97,328 or 3,341 and DD 268 955. The compounds of formula II are also known or can be prepared according to known processes.

The compounds of formula I are either known therapeutically-active compounds, or known intermediates for preparing therapeutically-active compounds.

In the following examples, there are described several preferred embodiments to illustrate the invention. However, it should be understood that the invention is not intended to be limited to the specific embodiments.

EXAMPLE I $\Delta^4$-pregnene-17α-ol-3, 11, 20 trions

Step A: 9 α-bromo-$\Delta^4$-pregene-11β, 17α-diol-3,20-dione 2 g of $\Delta^{4,9(11)}$-pregnadiene -17α-ol-3, 20-dione and 10 ml of tetrahydrofuran were mixed together under an inert gas atmosphere and then 1.3 g of N-bromosuccinimide were added at 0° C. The mixture was cooled to −3° C. and then a mixture of 1.3 ml of 65% perchloric acid and 2.5 ml of water was slowly added. The medium was stirred for 3 hours 30 minutes and then was poured into 100 ml of a water-ice mixture. The crystals were filtered off, washed with water and dried to obtain 2.5 g of the expected product which was used as is for the next step.

Step B: $\Delta^4$-pregnene-17α-ol-3, 11, 20 trions 2.05 g of the product of Step A, 14 ml of ethyl acetate and 4.6 ml of ethylene glycol were mixed together under an inert gas atmosphere and the mixture was refluxed for 16 hours and then was cooled to 20° C. 3.2 ml of concentrated hydrochloric acid and 35 ml of water were added and the mixture was stirred for 20 hours. The ethyl acetate was distilled off under reduced pressure and 7 g of sodium chloride were added. The mixture was stirred for 30 minutes at 20° C. and then the crystals were separated off and washed with salt water. The product was taken up in methylene chloride and the solution was dried and concentrated to dryness. The residue was chromatographed on silica, eluting with a methylene chloride-ethyl acetate mixture (8-2) to obtain 1.26 g of the expected product.
IR Spectrum ($CHCl_3$):
Absorptions at 3610 $cm^{-1}$ (OH); 1706–1667 $cm^{-1}$ (conjugated ketone); 1617 $cm^{-1}$ (C=C).

EXAMPLE 2 17α-acetoxy Δ4-pregnene-3,11,20-trione

Step A:
9α-bromo-17β-acetoxy-$\Delta^4$-pregnene-11β-ol-3,20-dione 3.7 g of 17α-acetoxy-$\Delta^{4,9(11)}$-pregnadiene-3,20-dione and 18.5 ml of tetrahydrofuran were mixed together under an inert gas atmosphere and after the mixture was cooled to 0° to 5° C., 2.18 g of N-bromosuccinimide were added. Then a mixture of 1.7 ml of 70% perchloric acid and 3.4 ml of water was slowly added and the mixture was stirred for one hour and then poured into 100 volumes of a water-ice mixture. The crystals were filtered off, washed with water and dried to obtain 4.82 g of the expected product.
IR Spectrum ($CHCl_33$):
Absorptions at 3612 $cm^{-1}$ (OH); 1731 $cm^{-1}$ (0Ac); 1716 and 1354 $cm^{-1}$ (—CO—$CH_3$); 1662 and 1621 $cm^{-1}$ (Δ4,3-one).

Step B: 17 g-acetoxy-$\Delta^4$-pregnene-3,11,20-trione

A mixture of 1 g of the product of Step A, 7 ml of ethyl acetate and 2.3 ml of ethylene glycol was refluxed under an inert gas atmosphere for 24 hours and after it was cooled to 20° C., 16 ml of concentrated hydrochloric acid and 17.5 ml of water were added. The mixture was stirred for 16 hours and then the ethyl acetate was distilled off under reduced pressure. Saturation was carried out with sodium chloride followed by extraction with methylene chloride. The organic phase was washed with a saturated aqueous solution of sodium bicarbonate, then with water saturated with sodium chloride and dried. After concentrating to dryness, the residue was chromatographed on silica, eluting with a methylene chloride-ethyl acetate mixture (9-1) to obtain 0.51 g of the expected product which was crystallized from ethanol.

IR Spectrum (CHCl$_3$):

Absorptions at 1735 cm$^{-1}$ (—OAc); 1708 cm$^{-1}$ (11 and 20 keto); 1668 and 1618 cm$^{-1}$ ($\Delta$4,3-one).

NMR Spectrum (CDCl$_3$, 250 MHZ, ppm): 0.63 (s): 18-CH$_3$; 1.42 (s): 19-CH$_3$; 2.03 (s) and 2.15 (s): CO-CH$_3$; 5.74 (s): H$_4$.

EXAMPLE 3 21-acetoxy $\Delta^4$-pregnene-17α ol-3, 11, 20-trione

Step A:
9α-bromo-21-acetoxy-$\Delta^4$-pregnene-11β-17α-diol-3,20-dione 4.71 g of 21-acetoxy-$\Delta$4,9(11) pregnadiene-17α-ol-3,20-dione and 65 ml of tetrahydrofuran were mixed together under an inert gas atmosphere and then at 0° to −5° C., 3.26 g of N-bromosuccinimide were added. Then, slowly, a mixture of 2.6 ml of 70% perchloric acid and 5.2 ml of water was added. After 75 minutes of stirring at 0° to −5° C., the solution was poured into 50 volumes of a water-ice mixture. Filtration was carried out and the crystals were washed with water, then dried to obtain 5.89 g of the expected product.

IR Spectrum (CHCl$_3$):

Absorptions at 1743–1722 cm$^{-1}$ (—CO—CH$_2$OAc); 1628 cm$^{-1}$ ($\Delta$4,3-keto); complex absorption (OH/NH) region Step B:
21-acetoxy-$\Delta^4$-pregnene-17α-ol-3,11,20-trione 0.7 g of the product of Step A, 4.9 ml of ethyl acetate and 1.6 ml of ethylene glycol were mixed together under an inert gas atmosphere and the mixture was refluxed for 5 hours and 15 minutes, then cooled to 20° C. 1.1 ml of concentrated hydrochloric acid and 12.2 ml of water were added and the mixture was stirred for 16 hours. Then, the ethyl acetate was distilled off under reduced pressure and the aqueous phase was saturated with sodium chloride. The crystals were separated off, washed with water saturated with sodium chloride, then dried. The product was taken up in a chloroform-isopropanol mixture (97-3), filtered and the filtrate was chromatographed on silica, eluting with a chloroform isopropanol mixture (97-3) to obtain 0.23 g of the expected product.

IR Spectrum (CHCl$_3$):

Absorptions at 3610 cm$^{-1}$ (—OH); 1748, 1730, 1707 and 1667 cm$^{-1}$ (C=O).

EXAMPLE 4 $\Delta^4$-pregnene-17α, 21-diol-3, 11, 20-trione

Step A: 9α-bromo-$\Delta^4$-pregnene-11β, 17α, 21-triol-3,20-dione 4.2 g of $\Delta$4,9(11)-pregnena-dien-17α,21-diol-3,20-dione and 46 ml of tetrahydrofuran were mixed together under an inert atmosphere at 0° to −5° C. and 3.26 g of N-bromosuccinimide were added to the mixture. Then, slowly, a mixture of 2.6 ml of 70% perchloric acid and 5.2 ml of water was added. After 75 minutes at 0° to −5° C., the solution was poured into 50 volumes of a water-ice mixture. Filtration was carried out and the crystals were washed and dried to obtain 4.86 g of the expected product.

IR Spectrum (Nujol):

Absorptions at 1710 cm$^{-1}$ (non-conjugated ketone), 1663 and 1618 cm$^{-1}$ (conjugated ketone), absorption OH/NH region.

Step B: $\Delta$4,-pregnene-17α,21-diol-3,11,20-trione 0.7 g of the product of Step A, 4.9 ml of ethyl acetate and 1.6 ml of ethylene glycol were mixed together under an inert gas atmosphere and the mixture was refluxed for 5 hours and 15 minutes, then cooled to 20° C. 1.1 ml of concentrated hydrochloric acid and 12.2 ml of water were added and the mixture was stirred for 16 hours. Then, the ethyl acetate was distilled off under reduced pressure and saturation was carried out with sodium chloride. The organic phase was washed with a saturated aqueous solution of sodium bicarbonate, then with a saturated aqueous solution of sodium chloride, dried and concentrated to dryness. The residue was chromatographed on silica, eluting with a chloroform-isopropanol mixture (92.5-7.5) to obtain 0.11 g of the expected product which was purified by dissolution in a methylene chloride-isopropyl ether mixture and distillation of the methylene chloride. The expected product crystallized.

IR Spectrum (Nujol):

Absorptions at 3480 cm$^{-1}$ (—OH); 1700 cm$^{-1}$ (11 and 20 keto); 1650 cm$^{-1}$ (conjugated ketone); 1613 cm$^{-1}$ (C=C)

Various modifications of the process of the invention may be made without departing from the spirit or scope thereof and it is to be understood that the invention is intended to be limited only as defined in the appended claims.

What we claim is:

1. A process for the preparation of a compound of the formula

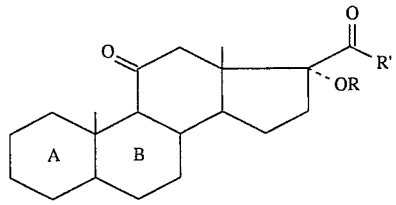

wherein R is selected from the group consisting of hydrogen, acyl of an organic carboxylic acid of 1 to 8 carbon atoms, tetrahydropyranyl, trialkylsilyl, triarylsilyl, diarylalkylsilyl and alkyl of 1 to 6 carbon atoms, R' is methyl or —CH$_2$ OR", R" is hydrogen or acyl of an organic carboxylic acid of 1 to 6 carbon atoms, tetrahydropyranyl, trialkylsilyl, triarylsilyl, diarylalkylsilyl or alkyl of 1 to 6 carbon atoms the same as or different from R, rings A and B are

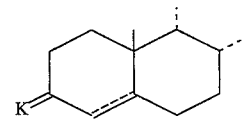

K=C is selected from the group consisting of

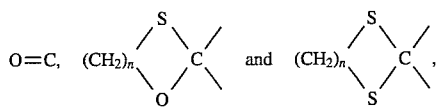

n is 2 or 3 and the dotted line is an optional bond comprising reacting a compound of the formula

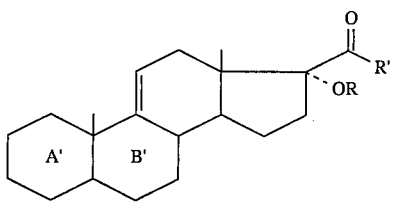

wherein R and R' have the above definitions and A' and B' are selected from the group consisting of A and B as above,

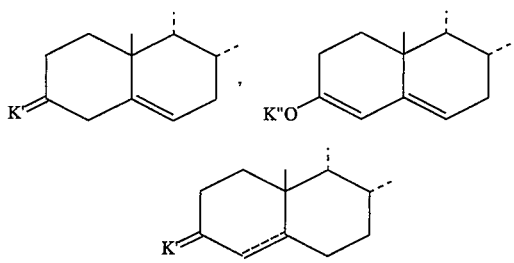

K' is

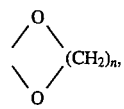

n is 2 or 3 and K" is alkyl of 1 to 8 carbon atoms or aryl of 6 to 12 carbon atoms with a halogenating agent to form a compound of the formula

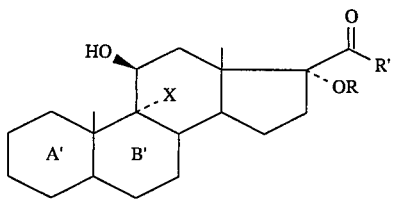

wherein R, R', A' and B' have the above definition and X is halogen, subjecting the compound of formula III to a rearrangement in the presence of an alcohol solvent to form the corresponding 11-oxo compound and then to an acid treatment to obtain a compound of formula I.

2. The process of claim 1 wherein the rearrangement is effected in the presence of an excess of a higher alcohol or a polyalcohol.

3. The process of claim 2 wherein the alcohol is selected from the group consisting of glycerol, ethylene glycol and propylene glycol.

4. The process of claim 1 wherein the rearrangement is effected in the presence of ethylene glycol.

5. The process of claim 1 wherein the rearrangement is effected with heating at a temperature below 100° C.

6. The process of claim 1 wherein the rearrangement is effected in the presence of a cosolvent with a boiling point less than 100° C. and is effected at reflux of the cosolvent.

7. The process of claim 6 wherein the cosolvent is ethyl acetate.

8. The process of claim 1 wherein X is bromine.

9. The process of claim 1 wherein A' and B' are

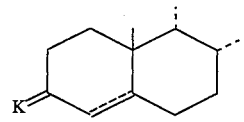

wherein K and the dotted line have the definition as defined in claim 1.

* * * * *